United States Patent [19]
Smith

[11] Patent Number: 6,159,737
[45] Date of Patent: Dec. 12, 2000

[54] METHOD OF ENHANCING THE RATE OF TRANSFECTION OF CELLS

[76] Inventor: John Arthur Smith, 13 St. Anthony's Road Blundellsands, Liverpool, United Kingdom, L23 8TN

[21] Appl. No.: 09/331,291

[22] PCT Filed: Dec. 19, 1997

[86] PCT No.: PCT/GB97/03457

§ 371 Date: Sep. 27, 1999

§ 102(e) Date: Sep. 27, 1999

[87] PCT Pub. No.: WO98/28432

PCT Pub. Date: Jul. 2, 1998

[30] Foreign Application Priority Data

Dec. 20, 1996 [GB] United Kingdom ............... 9626539

[51] Int. Cl.$^7$ ..................................................... C12N 15/64
[52] U.S. Cl. ..................... 435/455; 435/320.1; 530/399
[58] Field of Search ................................ 435/455, 320.1; 530/399

[56] References Cited

FOREIGN PATENT DOCUMENTS

| 0 273 085 | 7/1988 | European Pat. Off. . |
| WO 94/16737 | 8/1994 | WIPO . |
| WO 94/23751 | 10/1994 | WIPO . |
| WO 95/26718 | 10/1995 | WIPO . |
| WO 96/30536 | 10/1996 | WIPO . |

OTHER PUBLICATIONS

Boettger et al, "Condensation Of Vector DNA by the Chromosomal Protein HMG1 Results in Efficient Transfection" *Biochimica Et Biophysica Acta,* 950(2):221–228 (1988).

Boettger et al., "Transfection by DNA–Nuclear Protein HMG1 Complexes: Raising the Efficiency And Role of DNA Topology", *Archiv Fuer Geschwulstforschung,* 60(4):265–270 (1990).

Cristiano et al., "Epidermal Growth Factor Mediated DNA Delivery Into Lung Cancer Cells Via the Epidermal Growth Factor Receptor", *Cancer Gene Therapy,* 3(1):4–10 (1996).

Kaneda et al., "Increased Expression of DNA Cointroduced With Nuclear Protein in Adult Rat Liver", *Journal of Molecular Medicine,* 73(6):289–297 (1995).

*Primary Examiner*—James Ketter
*Attorney, Agent, or Firm*—Townsend and Townsend and Crew LLP

[57] ABSTRACT

The invention relates to a method of enhancing the rate of transfection of cells, a method of inserting genetic material into a cell in gene therapy and to a kit containing the components therefor. The method comprises stimulating the cells to be transfected with a growth regulating agent at about the time of transfection. Suitable growth regulating agents include growth promoting agents more particularly still growth factors such as EGF, FGF and NGF.

17 Claims, 2 Drawing Sheets

METHOD OF ENHANCING THE RATE OF TRANSFECTION OF CELLS

The present invention relates to a method of enhancing the rate of transfection of cells, to a kit containing the components therefore and to applications in gene therapy.

The rate of uptake of DNA into cells, and hence the efficiency of transfection of cells, is dependent on presenting the DNA in a suitably packaged form for uptake, traditionally by co-precipitation with calcium phosphate, and the ability of the cells to incorporate the packaged DNA into their cytoplasm.

A paper by Böttger et al, Biochemical et Biophysica Acta 950 (1988) 221–228, describes condensation of vector DNA by chromosomal protein HMG1. The method resulted in enhanced transfection.

It is an aim of the present invention to provide alternative methods of enhancing transfection which methods could, as well as being of benefit for transfection of cells in culture, give rise to applications in gene therapy.

The applicants have determined that increased efficiency of transfection can be obtained by stimulating the cell membrane with a growth regulating agent, leading to receptor mediated endocytosis, and that the increase in the rate of transection is at least as great as that resulting from enhanced packaging of DNA with HMG1.

According to a first aspect of the present invention there is provided a method of enhancing the rate of transfection of cells comprising stimulating the cells to be transfected with a growth regulating agent prior to transfection.

Preferably the growth regulating agent is a growth promoting agent, more particularly still a growth factor.

An advantage of using a growth regulating agent is that they can be selected to be specific or non-specific.

Thus, Epidermal Growth Factor (EFG), in spite of its name, will stimulate almost any cells of endothelial or epithelial origin, Fibroblast Growth Factor (FGF) stimulates cells of mesothelial origin and Nerve Growth Factor (NGF) has a very narrow specificity for neuronal cells. The specificity is dictated by the presence of specific receptors for the growth factors on the cell membrane.

This specificity may be particularly advantageous when it comes to consider gene therapy applications.

This is because a major problem to be overcome with gene therapy is how to achieve high rates of transfection with some specificity. Some present approaches can achieve physical localisation of the delivered gene, for instance to a specific organ. The methodology of the invention would, however, allow the selective targetting of a particular cell type within that organ, in addition to enhancing the overall level of transfection.

Other advantages over prior art methods are the cost benefit and the possibility of avoiding introducing "foreign" matter (e.g. viral matter)

As well as growth factors, other growth regulating agents such as, for example, Peanut Agglutinin and Mushroom Lectin could be used.

Lectin Peanut Agglutin is, for example, thought to promote the growth of cells by interaction with surface glycoproteins. In contrast Mushroom (Agaricus bisporis) Lectin, which shares the specificity of peanut agglutinin, is inhibiting to the growth of cells. Mushroom Lectin is found to be carried within the cell to the surface of the nuclear membrane and may possibly carry the DNA with it though the cell membrane. It is thus envisaged that, for example, a combination of a growth factor such as EGF with mushroom lectin would allow the enhancing effects of the growth promotion to be used for gene therapy without the possible disadvantage of the growth promoting effect in vivo.

In accordance with a further aspect of the present invention there is provided a method of inserting genetic material into a cell in gene therapy comprising stimulating the cell into which genetic material is to be inserted with a growth regulating agent in the presence of a growth inhibitor.

According to yet a further aspect of the present invention there is provided a kit for the methods of the invention comprising at least one growth regulating agent; and a buffer.

The Growth regulating agent should be present in an effective amount. For EGF an effective amount has been determined to be 1 $\mu$g /ml, although other amounts, for example, 0.1 $\mu$g to 10 $\mu$g may be used.

Optionally the kit also comprises one or more of the following: a precipitant, for example, $CaCl_2$ and/or HMG1, a plasmid control, e.g. PSV2neo, a marker e.g. genticin and a set of instructions.

Preferably the growth regulating agent is one or more of EGF, FGF, NGF, PDGF, IGF1, lectin peanut agglutinin and mushroom lectin.

Preferably the buffer is a HBS buffer comprising, for example, 280 mM NaCl, 50 mM HEPES and 1.5 mM $Na_2HPO_4$.

BRIEF DESCRIPTION OF THE DRAWINGS

FIG. 1 is a graph showing the transfection rate for:

1. EGF and HMG1
2. EGF alone
3. HMG1 alone
4. Calcium phosphate (Control), and
5. No Calcium phosphate.

Figure 2:
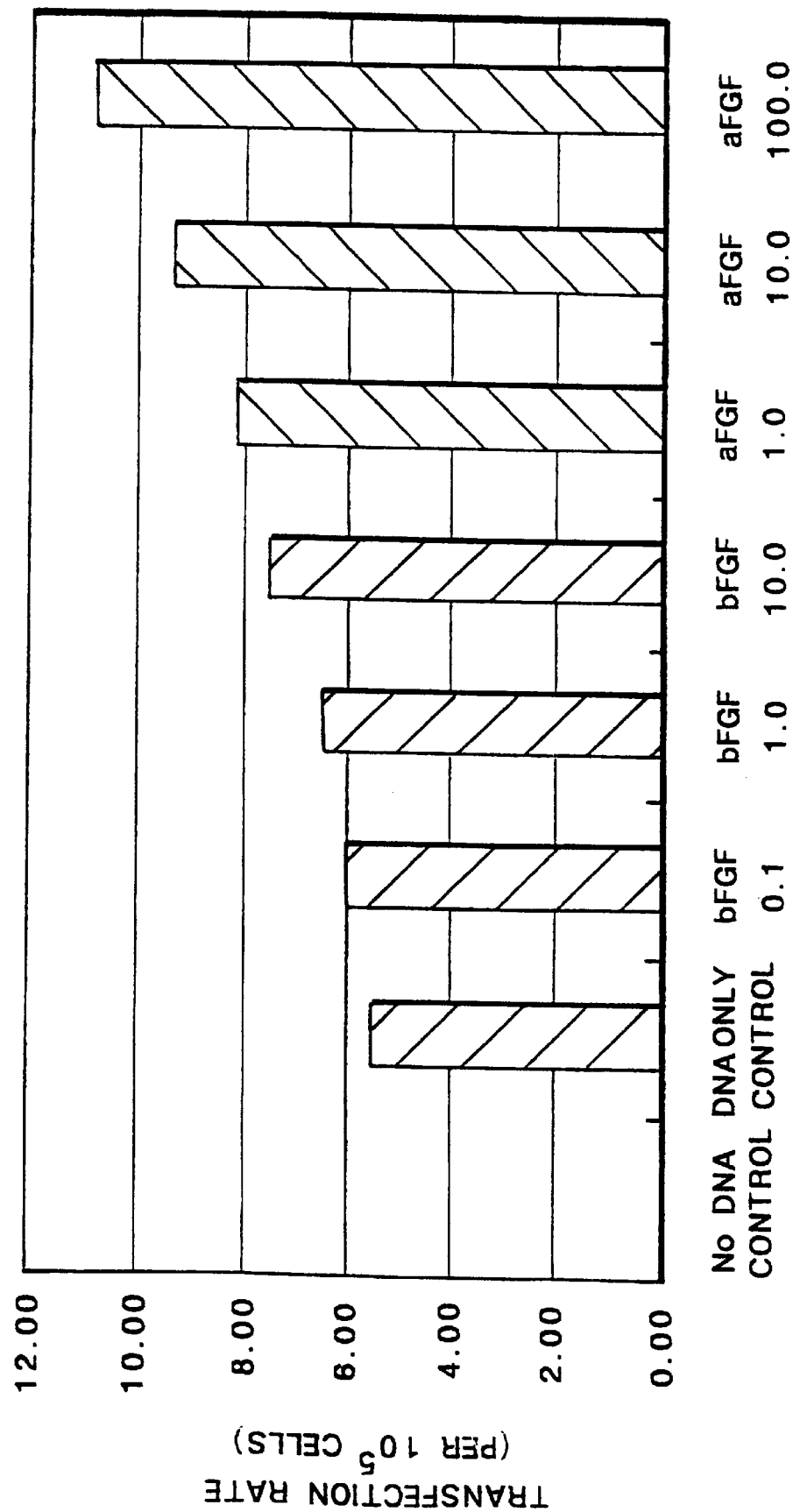

FIG. 2 is a graph showing transfection rates at different concentrations of FGF. FIG. 2 shows that transfection by DNA is increased by both acidic and basic FGF.

The invention will be further described by way of example only with reference to the following example.

METHOD

Cells and Growth Regulating Agents.

A rat mammary (Rama) cell line was cultured in Routine Medium (Dulbecco's Modified Eagle's Medium (Gibco, Paisley, UK) supplemented with 5% foetal calf serum (Biological Industries, Glasgow, UK), 50 ng/ml insulin, and 50 ng/ml hydrocortisone (Sigma, Pool, UK). The Rama 27 cell line was originally derived form the fast sticking fraction of cells isolated from a normal rat mammary gland and was defined as fibroblast on the basis of its ability to differentiate to the adipocyte phenotype (Rudland, P. S. et al (1984) J. Cell. Physiol. 120, 364–376). Epidermal group factor (EGF) was purified from mouse submandibular glands (Smith, J. A. et al (1984) J. Chromatogr. 305, 295–308).

Transfection

Rama 27 cells were passaged into 50mm dia, plates at a density of approximately $0.9 \times 10^6$ cells/plate, and incubated overnight at 37° C. The medium was changed 3 to 4 hours before transfection. Cells to be transfected were treated with 1 ml of a solution containing 500 $\mu$l 2×HBS and 125 $\mu$l 1M$CaCl_2$ and 375 $\mu$l $H_2O$, and a final concentration of 20 $\mu$g/ml pSV2neo (Graham, F. L. et al Virology 52, 456, 1973), together with other components as indicated. The plasmid and $CaCl_2$ were mixed using a peristaltic pump attached to a sterile siliconised Pasteur pipette. The suspension was allowed to stand for 30–45 min, inverted to mix and added directed to the culture medium. Growth factor, where appropriate was then added, and the plates were incubated at 37° C. for 4 hours. The medium was removed, replaced with normal medium containing 100% DMSO, and incubated for 90 sec. DMSO containing medium was removed, the cells were washed with routing medium, and incubated with fresh medium for 24 hours. Cells were plated at a density of $3\times10^5$ cells per 90 mm plate in medium containing 0.5 mg/ml geneticin initially, and subsequently, 1 mg/ml (selective medium). Selective medium was changed every 3 to 4 days during a 3 week period until colonies were clearly visible. The number of colonies was then counted. When used, HMG1 had a final concentration of 200 μg/ml (Böttger et al, (1988) Biochim. Biophys. Acta 950, 221–228) and EGF 10 ng/ml.

Results

TABLE 1

| Transfecting Agent | Growth Factor | CaPO$_4$ | No. of colonies | Transfection Rate (/10$^5$) |
|---|---|---|---|---|
| — | — | + | 0 | 0 |
| PSV2neo | — | + | 5 | 1.7 |
| PSV2neo | EGF | + | 18 | 6 |
| PSV2neo/HMG1 | — | + | 16 | 5.3 |
| PSV2neo/HMG1 | — | − | 4 | 1.3 |

The cells were resistant to geneticin only after treatment with the transfecting agent, showing that the resistance was caused by the transfected neo gene.

From Table 1 above it is apparent that the best transfection rate was achieved when a growth regulator EGF was included.

The results suggest that the growth regulating agents have a significant role in enhancing the uptake of genetic material (genes plasmids, antisense DNA, oligonucleotides, etc.) into cells in culture or in vivo, presumably by enhancing the rate of infolding of the membrane of the cells.

The method is expected to have the advantage that it will be additive to other methods; e.g. the use of HMG1, which acts by packaging the DNA more attractively to the cells.

The method should convey a degree of specificity to the mode of delivery, in that for each type of tissue or cell, there will be a preference for the response to growth factor. Thus, for example, the genetic material might be released in a specific tissue by physical means, but directed to a particular cell type within that tissue by the use of a growth factor specific to that cell type in order to increase overall uptake and/or to reduce side effects caused by delivery to the wrong cells.

Because of its non-specific mechanism, the method should also have applicability to situations in which it is required to increase the uptake of peptides or other hydrophilic compounds into cells.

In a further study the effect of EGF and HMG 1 on transfection rates was investigated.

Figure 1:
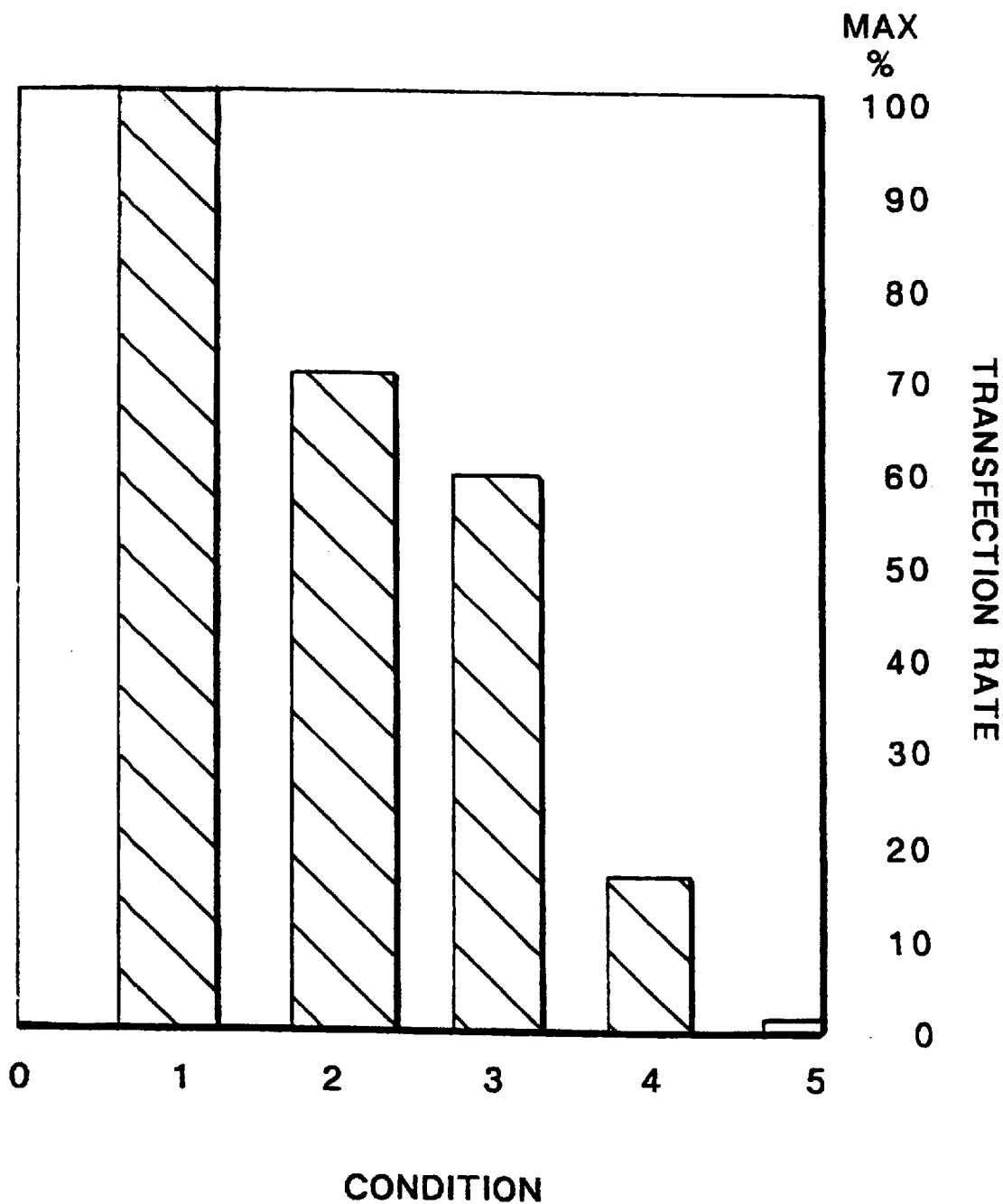

The results are shown in FIG. 1 which is a graph showing the transfection rate for:

1. EGF and HMG 1
2. EGF alone
3. HMG alone
4. Calcium phosphate (Control), and
5. No Calcium phosphate The results show EGF is significantly better than calcium phosphate (the current product) and that the case of EGF and HMG 1 together produce even better results.

These results support the applicants belief that EGF and HMG 1 act in different ways. The results are compatible with the idea that the growth factor enhances the rate of uptake in the cells whereas the HMG 1 protein binds DNA into a preferable conformation and transports it to the nucleus.

In yet a further study the effect of both acidic and basic FGF on transfection rates was investigated. The results are illustrated in FIG. 2 which is a graph showing transfection rates at different concentrations. FIG. 2 shows that transfection by DNA is increased by both acidic and basic FGF. Surprisingly the acidic FGF is better than the basic FGF because basic FGF is better than the acidic FGF when it comes to promoting growth of Rama 27 cells.

What is claimed is:

1. A method enhancing the rate of transfection of cells comprising stimulating the cells to be transfected with a free and unbound growth factor together with HMG 1 at about the time of transfection.

2. A kit for enhancing the rate of transfection of cells comprising a free and unbound growth factor together with HMG 1, and a buffer.

3. The kit of claim 2 further comprising a precipitant, a plasmid control, a selective agent, and a set of instructions.

4. The method of claim 1 wherein the growth factor is specific to the cells being transfected.

5. The method of claim 1 wherein the growth factor is non-specific to the cells being transfected.

6. The method of claim 1 in which the growth factor is epidermal growth factor (EGF).

7. The method of claim 1 in which the growth factor is fibroblast growth factor (FGF).

8. The method of claim 7, wherein the FGF is acidic FGF.

9. The method of claim 1 in which the growth factor is nerve growth factor (NGF).

10. The method of claim 1 in which the growth factor is platelet derived growth factor (PDGF).

11. The method of claim 1 in which the growth factor is insulin like growth factor 1 (IGF 1).

12. The method of claim 1 wherein a growth regulating agent is used in combination with the growth factor.

13. The method of claim 12 wherein the growth regulating agent is a lectin.

14. The method of claim 13 wherein the lectin is lectin peanut agglutinin.

15. The method of claim 13 wherein the lectin is a mushroom lectin.

16. A method of inserting genetic into a cell comprising stimulating the cell growth into which genetic material is to be inserted with a free and unbound growth factor together with HMG 1 in the presence of a growth inhibitor.

17. The method of claim 1 wherein the cells are in culture.

\* \* \* \* \*

UNITED STATES PATENT AND TRADEMARK OFFICE
CERTIFICATE OF CORRECTION

PATENT NO. : 6,159,737
DATED : December 12, 2000
INVENTOR(S) : John Arthur Smith It is certified that error appears in the above-identified patent and that said Letters Patent is hereby corrected as shown below:

The § 102(e) date should be -- June 18, 1999 --.

Signed and Sealed this

Sixth Day of November, 2001

*Attest:*

NICHOLAS P. GODICI
*Attesting Officer*     *Acting Director of the United States Patent and Trademark Office*